United States Patent [19]
Kudzma et al.

[11] Patent Number: 5,886,239
[45] Date of Patent: Mar. 23, 1999

[54] METHOD OF PREPARING MONOFLUOROMETHYL ETHERS

[75] Inventors: Linas V. Kudzma, Annandale; Ralph A. Lessor, New Providence; Leonid A. Rozov, Fair Lawn; Keith Ramig, Orange, all of N.J.

[73] Assignee: Baxter International Inc.

[21] Appl. No.: 975,689

[22] Filed: Nov. 21, 1997

[51] Int. Cl.$^6$ ...................................................... C07L 41/00
[52] U.S. Cl. ............................................ 568/684; 568/683
[58] Field of Search ...................................... 568/671, 681, 568/683, 684

[56] References Cited

U.S. PATENT DOCUMENTS

| | | | |
|---|---|---|---|
| 3,683,092 | 8/1972 | Regan et al. | 424/342 |
| 3,689,571 | 9/1972 | Regan et al. | 260/614 |
| 3,897,502 | 7/1975 | Russell et al. | 260/614 |
| 4,250,334 | 2/1981 | Coon et al. | 568/683 |
| 4,314,087 | 2/1982 | Radlick | 568/842 |
| 4,328,376 | 5/1982 | Berger et al. | 568/682 |
| 4,469,898 | 9/1984 | Coon et al. | 568/683 |
| 4,874,901 | 10/1989 | Halpern et al. | 568/683 |

FOREIGN PATENT DOCUMENTS

| | | |
|---|---|---|
| 25 20 962 | 12/1976 | Germany . |
| 28 23 969 | 12/1979 | Germany . |
| 2823969 | 12/1979 | Germany . |
| WO 97/25303 | 7/1997 | WIPO . |

OTHER PUBLICATIONS

Merck, citation for Sevoflurane, Merck Number 8621.
Bensoam et al. Tetrahedron Lett. (1979), (4), 353–356 (Abstract only provided).
Okazaki et al., Journal of Fluorine Chemistry, 4 (1974) 387–397.
Franz, Journal of Fluorine Chemistry, 15 (1980) 423–434.
Halpern, Organofluorine Chemistry: Principles and Commercial Applications, Banks et al. 1994, pp. 543–554.

*Primary Examiner*—Michael L. Shippen
*Attorney, Agent, or Firm*—R. Hain Swope; Jeffrey C. Nichols; Mark J. Buonaiuto

[57] ABSTRACT

A method of preparing fluoromethyl 2,2,2-trifluoro-1-(trifluoromethyl)ethyl ether (sevoflurane) and structurally related monofluoromethyl ethers in which the monochloromethyl ether precursor thereof is reacted with a sterically hindered tertiary amine hydrofluoride salt.

7 Claims, No Drawings

METHOD OF PREPARING MONOFLUOROMETHYL ETHERS

FIELD OF THE INVENTION

The present invention is directed to a method of preparing monofluoromethyl ethers, and in particular, fluoromethyl 2,2,2-trifluoro-1-(trifluoromethyl)ethyl ether (sevoflurane) in which yields of the desired products are improved over prior art methods.

BACKGROUND OF THE INVENTION

In recent years, fluorinated ethers have been discovered which have useful anesthetic properties via inhalation. Included among these anesthetics are desflurane ($CF_3CHFOCHF_2$), isoflurane ($CF_3CHClOCHF_2$), enflurane ($HClFCCF_2OCHF_2$), and sevoflurane (($CF_3$)$_2CHOCH_2F$). Sevoflurane is an advantageous inhalation anesthetic because of its rapid onset of anesthesia and rapid recovery, which are desirable characteristics of modern day inhalation anesthetics. Sevoflurane is administered by the inhalation route to warm-blooded, air-breathing animals in an amount of from about 1% to 5% by volume in admixture with oxygen or a gaseous mixture containing oxygen in an amount sufficient to support respiration.

U.S. Pat. Nos. 3,683,092 and 3,689,571 disclose the use of sevoflurane as an inhalation anesthetic and its synthesis by reaction of chloromethyl 2,2,2-trifluoro-1-(trifluoromethyl)ethyl ether with excess potassium fluoride in a high boiling solvent, sulfolane, at 120° C. to replace the chlorine of the chloromethyl group with fluorine. These patents also disclose a method of producing sevoflurane by reaction of hexafluoroisopropanol with dimethyl sulfate and sodium hydroxide solution, and subsequent fluorination of the resulting methyl 2,2,2-trifluoro-1-(trifluoromethyl)ethyl ether with bromine trifluoride. U.S. Pat. No. 4,328,376 discloses separation of sevoflurane from a by-product olefin produced in a process similar to that described in U.S. Pat. No. 3,689,571.

Other synthetic routes to sevoflurane are found in the following patent publications: U.S. Pat. No. 3,897,502—fluorination of methyl 2,2,2-trifluoro-1-(trifluoromethyl) ethyl ether with 20% fluorine in argon; U.S. Pat. Nos. 4,250,334 and 4,469,898—fluoromethylation of hexafluoroisopropanol utilizing hydrogen fluoride, formaldehyde and sulfuric acid or other dehydrating agents; U.S. Pat. No. 4,874,901—reaction of chloromethyl 2,2,2-trifluoro-1-(trifluoromethyl)ethyl ether with neat potassium fluoride under conditions of high temperature and pressure; and PTC Int. Appl. WO 97 25,303—reaction of hexafluoroisopropanol with bis(fluoromethyl)ether.

Okazaki, et. al. in J. Fluorine Chem. 1974, 4(4), 387 describe an electrochemical fluorination that gives a fluoromethyl ether. German Patent No. 25 20 962 describes a synthesis of fluoromethyl ethers from chloromethyl ethers with hydrogen fluoride at 125°–149° C. in the presence of chromium oxyfluoride. Bensoam, et. al. in Tetrahedron Lett. 1979, 4, 353 describe a synthesis of fluoromethyl ethers by halogen exchange with tetraalkylfluorophosphoranes. Finally, German Patent No. 28 23 969 discloses a process for preparing organofluorine compounds, including monofluoromethyl ethers, by reaction of corresponding organochlorides or bromides with selected amine hydrofluorides. Triethylamine hydrofluoride and piperidine hydrofluoride are specific examples of fluorinating agents used for the preparation of such organofluorine compounds, which are typically produced in yields of from about 40 to 80%.

In accordance with the present invention, a synthesis of certain monofluoromethyl ethers, in particular sevoflurane, is provided which is characterized by improved yields over previously known methods.

SUMMARY OF THE INVENTION

In accordance with the present invention, there is provided a method for the fluorination of certain monochloromethyl ethers with sterically hindered tertiary amine hydrofluoride salts to yield the corresponding monofluoromethyl ethers. More particularly, the invention is directed to a method of producing fluoromethyl 2,2,2-trifluoro-1-(trifluoromethyl)ethyl ether (sevoflurane-($CF_3$)$_2CHOCH_2F$) comprising reacting chloromethyl 2,2,2-trifluoro-1-(trifluoromethyl)ethyl ether with diisopropylethylamine hydrofluoride.

DETAILED DESCRIPTION OF THE INVENTION

The present invention is generally directed to a method for the fluorination of monochloromethyl ethers with sterically hindered tertiary amine hydrofluoride salts to give the corresponding monofluoromethyl ethers. The monochloromethyl ether starting materials of the present invention are known compounds and are represented by the general formula:

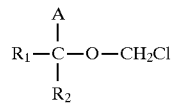

wherein A is fluoro lower alkyl, fluorine or chlorine and $R_1$ and $R_2$ are independently selected from hydrogen, lower alkyl, branched lower alkyl, fluoro lower alkyl, fluorine and chlorine with the stipulation that at least one of A, $R_1$ or $R_2$ is fluoro lower alkyl, lower alkyl or branched lower alkyl. Fluorination of the above monochloromethyl ethers with sterically hindered tertiary amine hydrofluoride salts give monofluoromethyl ethers represented by the formula:

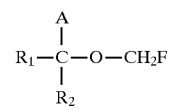

Wherein A, $R_1$ or $R_2$ are as defined above.

In a preferred embodiment, the present invention is directed to a method of producing fluoromethyl 2,2,2-trifluoro-1-(trifluoromethyl)ethyl ether (sevoflurane) by reacting chloromethyl 2,2,2-trifluoro-1-(trifluoromethyl) ethyl ether with a sterically hindered tertiary amine hydrofluoride salt.

Preferred sterically hindered tertiary amines usable in the method of the present invention are selected from those represented by the formula:

wherein X, Y, and Z are lower alkyl groups, at least one of which is a branched lower alkyl or cycloalkyl group. Examples of representative branched- or cyclo lower alkyl groups present in compounds of the above formula include isopropyl, tert-butyl, neopentyl, cyclohexyl and the like. In a preferred embodiment of the invention, the hindered tertiary amine is diisopropylethylamine.

The term "lower alkyl" as utilized herein means saturated alkyl groups containing 1 to 6 carbons and shall be straight-chain unless specifically stated otherwise. The term "fluoro lower alkyl" as utilized herein means saturated alkyl groups containing 1 to 6 carbons and substituted by at least one fluorine. A preferred fluoro lower alkyl group is trifluoromethyl.

The sterically hindered tertiary amine hydrofluoride salt utilized in the reaction of the present invention is actually formed in situ as will be recognized by those of ordinary skill in the art of fluorocarbon chemistry. While the reagent of the reaction described herein is referred to herein as the hydrofluoride salt, it is the use of the sterically hindered tertiary amines described which provide the improved yields of the subject synthesis. The hydrofluoride salts of the subject amines can be formed in situ by combining anhydrous hydrogen fluoride with about one molar equivalent of the sterically hindered tertiary amine, e.g. diisopropylethylamine. Alternately, a previously prepared stable sterically hindered tertiary amine tris-hydrogen fluoride complex can be added to the reaction mixture and treated with two molar equivalents of the free tertiary amine to form three molar equivalents of the sterically hindered tertiary amine hydrofluoride salt in situ. In accordance with the present invention, the sterically hindered tertiary amine hydrofluoride salt is combined with the monochloromethyl ether precursor, and the resulting mixture heated for an appropriate time sufficient to cause formation of the product monofluoromethyl ether.

The conversion of monochloromethyl ethers to monofluoromethyl ethers by heating with a sterically hindered tertiary amine hydrofluoride salt of the present invention can be conducted in the absence of a solvent, or in the presence of a solvent, for example, a high boiling inert solvent such as 1-methyl-2-pyrrolidinone, sulfolane or the like. In a preferred embodiment of the invention, the reaction is conducted without additional solvent utilizing an excess of the monochloromethyl ether reactant which advantageously also functions as the solvent. The conversion of monochloromethyl ethers to monofluoromethyl ethers in accordance with the present invention can be conducted at elevated temperatures, in the range of 50°–100° C., at atmospheric pressure or in a sealed pressure vessel. In a preferred embodiment of the invention, the reaction is conducted at the reflux temperature of the monochloromethyl ether.

The use of sterically hindered tertiary amine hydrofluoride salts for the conversion of monochloromethyl ethers to monofluoromethyl ethers in the present invention is a substantial improvement over the previous use of triethylamine hydrofluoride and piperidine hydrofluoride, as described in German Patent No. 28 23 969. The yields of the desired product obtained in the present invention are consistently superior to those obtained using the previously described amine hydrofluoride salts, as evidenced in the Examples provided hereinbelow. It has been demonstrated, in contrast to prior art amine hydrofluoride salts, those of the present invention are not alkylated to a degree in the reaction. The alkylation of the less hindered amine hydrofluoride salts of the prior art to form a quaternary ammonium salt as a reaction byproduct has heretofore not been described in the literature. The consistently superior yields obtained using the sterically hindered tertiary amines in the method of the invention are the result of avoidance of this heretofore undescribed side reaction.

The following examples further illustrate the subject invention, it being understood that it is in no way intended that the specifics given therein are to be limiting thereon.

EXAMPLE 1

Preparation of Fluoromethyl 2,2,2-trifluoro-1-(trifluoromethyl)ethyl ether with diisopropylethylamine hydrofluoride In an efficient fume hood, liquid hydrogen fluoride (85.1 g, 4.25 mol) was transferred into a 1 liter Teflon® reaction vessel chilled in a dry ice/acetone cold bath. The vessel was fitted with a dry ice condenser, thermocouple, and addition funnel and a portion of chloromethyl 2,2,2-trifluoro-1-(trifluoromethyl)ethyl ether (80.1 g) was added. A solution of diisopropylethylamine (249.0 g, 1.93 mol) in chloromethyl 2,2,2-trifluoro-1-(trifluoromethyl)ethyl ether (271.0 g) was slowly added while maintaining the internal temperature in the range of −5°to 10° C. After completing the addition, the mixture was transferred to a 2 liter glass boiling flask and the Teflon® vessel was rinsed out with a solution of diisopropylethylamine (307.0 g, 2.38 mol) in chloromethyl 2,2,2-trifluoro-1-(trifluoromethyl)ethyl ether (180.0 g) which was also transferred to the glass flask. An additional 850 g of chloromethyl 2,2,2-trifluoro-1-(trifluoromethyl) ethyl ether was added to the reaction flask to bring the total to 1381.1 g (6.38 mol). This mixture was heated at reflux for 16 hours. After cooling to ambient temperature, water (700 mL) was added to the reaction mixture and, after vigorous shaking, the resultant layers were separated. The lower organic layer was further washed with 700 mL of dilute hydrochloric acid (35 mL of 12 N HCl in 665 mL of water). The organic layer (1259.7 g) was analyzed by NMR and gas chromatography and was shown to consist of 63.6% fluoromethyl 2,2,2-trifluoro-1-(trifluoromethyl)ethyl ether (sevoflurane) and 35.4% recovered chloromethyl 2,2,2-trifluoro-1-(trifluoromethyl)ethyl ether, giving a 95% yield of sevoflurane based on starting material consumed.

EXAMPLE 2

Preparation of Fluoromethyl 2,2,2-trifluoro-1-(trifluoromethyl)ethyl ether with triethylamine hydrofluoride Triethylamine (5.0 g, 49.4 mmol) was added to a solution of triethylamine tris-hydrogen fluoride (4.0 g, 24.8 mmol) in chloromethyl 2,2,2-trifluoro-1-(trifluoromethyl)ethyl ether (32.28 g, 149.1 mmol). This mixture was heated at reflux for 16 hrs, during which time solids separated. The precipitate consisted of triethylamine hydrochloride and the undesired quaternary salt, (1,1,1,3,3,3-hexafluoroisopropoxymethyl) triethylammonium chloride, formed by the reaction of chloromethyl 2,2,2-trifluoro-1-(trifluoromethyl)ethyl ether with triethylamine. After cooling to ambient temperature, water (50 mL) was added to the reaction mixture and, after vigorous stirring to dissolve all solids, the lower organic layer was separated. The organic layer (27.98 g) was analyzed by NMR and gas chromatography and found to consist of 42.3% fluoromethyl 2,2,2-trifluoro-1-(trifluoromethyl) ethyl ether (sevoflurane) and 57.5% recovered chloromethyl 2,2,2-trifluoro-1-(trifluoromethyl)ethyl ether. This corresponds to a 79% yield of sevoflurane based on starting material consumed.

EXAMPLE 3

Preparation of Fluoromethyl 1,1,2,3,3,3-hexafluoropropyl ether with diisopropylethylamine hydrofluoride Diisopropylethylamine (56 mL, 320 mmol) was added to a solution of chloromethyl 1,1,2,3,3,3-hexafluoropropyl ether (98.8 g, 440 mmol, 96% purity) and diisopropylethylamine tris-hydrogen fluoride complex (30.7 g, 160 mmol) previously prepared by reaction of diisopropylethylamine with three molar equivalents of anhydrous hydrogen fluoride. The mixture was heated at reflux under $N_2$ for 12 h. Upon cooling, the mixture solidified. Water (100 mL) was added with rapid stirring. The lower layer was dried over $CaCl_2$, giving 83 g of a dark liquid. NMR analysis showed this liquid to be composed of 88% fluoromethyl 1,1,2,3,3,3-hexafluoropropyl ether, 8% recovered chloromethyl 1,1,2,3,3,3-hexafluoropropyl ether, and 4% dichloromethyl 1,1,2,3,3,3-hexafluoropropyl ether, an impurity present in the starting chloromethyl ether. Distillation yielded 64 g of fluoromethyl 1,1,2,3,3,3-hexafluoropropyl ether as a clear colorless liquid (bp 68° C.) in 78% yield based on the amount of starting material consumed. Use of triethylamine hydrofluoride under otherwise identical reaction conditions gave a significantly lower yield (52%) of the desired fluoromethyl ether.

EXAMPLE 4

Preparation of Fluoromethyl 1,2,2,2-tetrafluoroethyl ether utilizing diisopropylethylamine hydrofluoride Diisopropylethylamine (6.97 mL, 40.0 mmol) was added to a solution of chloromethyl 1,2,2,2-tetrafluoroethyl ether (9.99 g, 60.0 mmol) and diisopropylethylamine tris-hydrogen fluoride (3.78 g, 20.0 mmol), previously prepared by reaction of diisopropylethylamine with three molar equivalents of anhydrous hydrogen fluoride. The mixture was heated at reflux under $N_2$ for 10 h. Upon cooling, the mixture was a well-dispersed slurry. Ice-cold water (10 mL) was added with rapid stirring. The lower layer was dried over $CaCl_2$, giving 8.44 g of a yellowish liquid. NMR analysis showed this liquid to consist of 73% fluoromethyl 1,2,2,2-tetrafluoroethyl ether, 18% recovered chloromethyl 1,2,2,2-tetrafluoroethyl ether, and 7% diisopropylethylamine hydrochloride. This corresponds to a 81% yield of the desired fluoromethyl ether based on starting material consumed. Use of triethylamine hydrofluoride under otherwise identical reaction conditions gave a significantly lower yield (35%) of the desired fluoromethyl ether.

What is claimed is:

1. A method for the preparation of a monofluoromethyl ether represented by the formula:

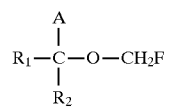

wherein A is fluoro lower alkyl, fluorine or chlorine and $R_1$ and $R_2$ are independently selected from the group consisting of hydrogen, lower alkyl, branched lower alkyl, fluoro lower alkyl, fluorine and chlorine with the proviso that at least one of A, $R_1$ or $R_2$ is fluoro lower alkyl, lower alkyl or branched lower alkyl, by the reaction of the corresponding monochloromethyl ether with a sterically hindered tertiary amine hydrofluoride salt.

2. A method in accordance with claim 1, wherein the sterically hindered tertiary amine is represented by the formula

wherein X, Y, and Z are independently selected from the group consisting of lower alkyl, branched lower alkyl and cyclolower alkyl, with the proviso that at least one of which consists of a branched lower alkyl or cycloalkyl group.

3. A method in accordance with claim 2, wherein X is an ethyl group and each of Y and Z is an isopropyl group.

4. A method in accordance with claim 1, wherein said monofluoromethyl ether is fluoromethyl 2,2,2-trifluoro-1-(trifluoromethyl)ethyl ether, said monochloromethyl ether is chloromethyl 2,2,2-trifluoro-1-(trifluoromethyl)ethyl ether and said sterically hindered tertiary amine hydrofluoride salt is diisopropylethylamine hydrofluoride salt.

5. A method in accordance with claim 1, wherein said reaction is carried out in the presence of a solvent.

6. The method of claim 5, in which the reaction is carried out at the reflux temperature of the reaction mixture.

7. A method in accordance with claim 4, wherein the reaction is carried out using an excess of the chloromethyl ether starting material relative to the amount of the diisopropylethylamine hydrofluoride salt, in the absence of added solvent.

* * * * *